(12) United States Patent
Payne et al.

(10) Patent No.: US 8,483,458 B2
(45) Date of Patent: *Jul. 9, 2013

(54) METHOD AND SYSTEM FOR MEASURING VISCERAL FAT MASS USING DUAL ENERGY X-RAY ABSORPTIOMETRY

(75) Inventors: Randall K. Payne, Madison, WI (US); David Ergun, Verona, WI (US); James A. Wear, Madison, WI (US); Wynn K. Wacker, Madison, WI (US); Howard S. Barden, Madison, WI (US)

(73) Assignee: General Electric Company, Schenectady, NY (US)

( * ) Notice: Subject to any disclaimer, the term of this patent is extended or adjusted under 35 U.S.C. 154(b) by 196 days.

This patent is subject to a terminal disclaimer.

(21) Appl. No.: 12/982,952

(22) Filed: Dec. 31, 2010

(65) Prior Publication Data

US 2011/0158386 A1 Jun. 30, 2011

Related U.S. Application Data

(63) Continuation-in-part of application No. 12/557,285, filed on Sep. 10, 2009.

(51) Int. Cl.
*G06K 9/00* (2006.01)

(52) U.S. Cl.
USPC .............................. 382/128; 128/922; 378/4

(58) Field of Classification Search
USPC .. 382/100, 128, 129, 130, 131, 132; 128/922; 378/4–27

See application file for complete search history.

(56) References Cited

U.S. PATENT DOCUMENTS

| | | | |
|---|---|---|---|
| 6,198,797 B1 * | 3/2001 | Majima et al. | 378/98 |
| 6,752,760 B2 * | 6/2004 | Kouou | 600/301 |
| 6,850,797 B2 * | 2/2005 | Kawanishi et al. | 600/547 |
| 6,978,170 B1 * | 12/2005 | Onda et al. | 600/547 |
| 7,725,153 B2 * | 5/2010 | Kelly et al. | 600/407 |
| 2010/0234719 A1 * | 9/2010 | Kelly et al. | 600/407 |
| 2010/0278405 A1 * | 11/2010 | Kakadiaris et al. | 382/131 |

* cited by examiner

*Primary Examiner* — Anand Bhatnagar
(74) *Attorney, Agent, or Firm* — William Baxter; Patrick J. Kim (57) ABSTRACT

Methods and system for measuring visceral fat mass are provided. One method includes acquiring dual-energy two-dimensional (2D) scan information from a dual-energy X-ray scan of a body and generating a dual-energy X-ray image of the body using the 2D scan information. The method further includes identifying a region of interest using the dual-energy X-ray image and determining a subcutaneous fat mass for each of a plurality of sections of the region of interest. The method also includes determining a visceral fat mass for the region of interest based on the determined subcutaneous fat mass for each of the plurality of sections.

22 Claims, 7 Drawing Sheets

METHOD AND SYSTEM FOR MEASURING VISCERAL FAT MASS USING DUAL ENERGY X-RAY ABSORPTIOMETRY

CROSS-REFERENCE TO RELATED APPLICATIONS

This application is a continuation-in-part of and claims priority to U.S. patent application Ser. No. 12/557,285, filed on Sep. 10, 2009, the disclosure of which is incorporated herein by reference.

BACKGROUND OF THE INVENTION

This disclosure relates generally to medical diagnostic imaging methods and systems, and more particularly to medical diagnostic imaging methods and systems that acquire and process tissue information for measuring the visceral fat mass of an individual.

Characteristics of an individual, such as body weight, fat mass, height, gender, age, etc. are clinical descriptors useful by physicians to predict certain health risks that may increase or decrease mortality and morbidity risk. For example, the amount or type of abdominal fat, such as subcutaneous adipose tissue (SAT) or subcutaneous fat and visceral adipose tissue (VAT) or visceral fat are associated with, and useful predictors of, an adverse metabolic risk profile and certain diseases, such as coronary heart disease and diabetes. In addition, measuring visceral fat, for example, can relate to metabolic syndrome (i.e., a combination of medical problems that can increase the risk of heart disease and/or diabetes). People suffering from metabolic syndrome can have some or all of the following: high blood glucose, high blood pressure, abdominal obesity, low high-density lipoprotein (HDL) cholesterol, high low-density lipoprotein (LDL) cholesterol, high total cholesterol and/or high triglycerides.

Conventional methods and systems for measuring VAT are mostly performed using anthropomorphic gauges, bioimpedance gauges, weight scales, etc. These devices often are not capable of providing accurate measurements of VAT because the actual fat content is not being measured, certain assumptions/estimates are made during the calculation process, and/or the devices are not exactly calibrated. Also, reproducibility may be difficult, leading to inaccurate comparisons between examinations.

Medical diagnostic imaging systems have also been used to measure VAT content. However, the use of these systems are often costly and can expose a patient to high levels of ionizing radiation, for example, when using a computed tomography (CT) imaging system. Additionally, these imaging systems are not always available for clinical use and may have long scan times. Moreover, certain measurements are inaccurate in larger individuals.

Conventional methods and systems for determining VAT often also use simple models to approximate the abdominal cavity from an estimate of subcutaneous fat thickness measurements. However, these methods and systems often fail to accurately estimate SAT, thereby resulting in an inaccurate estimate of VAT. For example, a normal dual-energy X-ray absorptiometry (DXA) image of the abdomen is a planar two-dimensional (2D) image that cannot explicitly measure VAT because it cannot measure the thickness of SAT in the vertical plane. It has been very difficult to determine the thickness of the subcutaneous fat layer around the abdomen, especially near the buttocks, since the models used in the past do not take into account differences in the thickness of the subcutaneous fat layer around the abdomen near the buttocks.

Therefore, there is a need for a method and system to more accurately measure VAT using DXA by measuring and correcting for SAT composition.

BRIEF DESCRIPTION OF THE INVENTION

In accordance with an aspect of the disclosure, a method for determining visceral fat mass of a body, the method comprising performing a dual-energy X-ray scan of a body; generating at least one dual-energy X-ray image of the body from the dual-energy X-ray scan of the body; identifying a region of interest on the at least one dual-energy X-ray image of the body for determining visceral fat mass of the body; determining a subcutaneous fat mass for each of a plurality of sections of the region of interest; and determining a visceral fat mass for the region of interest based on the determined subcutaneous fat mass for each of the plurality of sections.

In accordance with an aspect of the disclosure, a method for determining visceral fat mass of an abdominal region of a body, the method comprising acquiring body composition information using a planar dual-energy X-ray imaging system, and segmenting visceral fat in the abdominal region using the acquired body composition information to determine the visceral fat mass of the body.

In accordance with an aspect of the disclosure, a diagnostic imaging system comprising a dual-energy X-ray bone densitometry system configured to acquire body composition information from a dual-energy X-ray scan of a subject, and a body fat measurement module configured to segment visceral fat in an abdominal region of the subject to determine an amount of visceral fat mass in the abdominal region using the body composition information.

Various other features, aspects, and advantages will be made apparent to those skilled in the art from the accompanying drawings and detailed description thereof.

DETAILED DESCRIPTION OF THE INVENTION

Exemplary embodiments of dual-energy X-ray imaging methods and systems for scanning bodies to obtain or determine tissue information, particularly soft tissue information, such as visceral adipose tissue information, are described in detail below. Various embodiments calculate or estimate abdominal visceral fat mass using dual-energy X-ray absorptiometry (DXA). At least one technical effect of the various embodiments of the systems and methods described herein is to determine visceral fat mass in the abdominal region of a subject using a soft tissue composition profile acquired from a DXA scan. Different methods, systems and models are used to measure the visceral fat mass of a subject in different regions of the subject's body.

Figure 1:
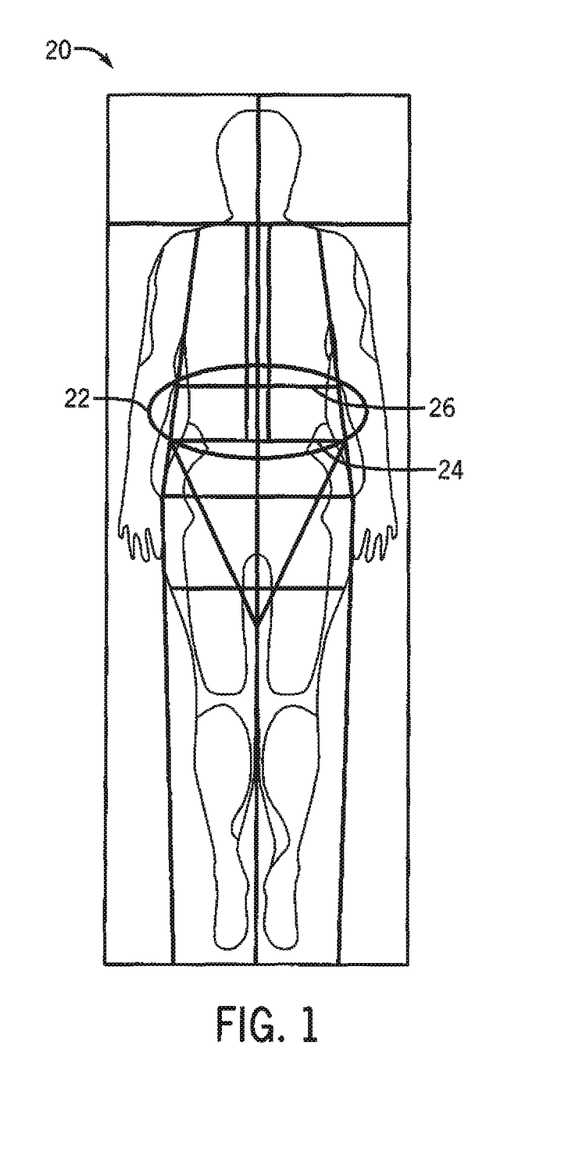
FIG. 1 is a diagram of an exemplary embodiment of a dual-energy X-ray image identifying an abdominal region of interest to determine an abdominal visceral fat mass of a subject.

Referring now to the drawings, FIG. 1 illustrates a diagram of an exemplary embodiment of a dual-energy X-ray image 20 of a body (e.g., a subject's body), and more particularly, a full body dual-energy X-ray image 20 that may be generated from a scan of the entire body of a subject using a dual-energy X-ray imaging system. The illustrated dual-energy X-ray image 20 is a dual-energy tissue image. The image 20 is generated from a full body scan, which in some embodiments includes acquiring all bone and tissue information during a single scan, for example, a single imaging pass or operation. The total body scan may be acquired using different dual-energy X-ray imaging systems, for example, the Lunar iDXA imaging system available from GE Healthcare or other bone densitometry systems. The Lunar iDXA imaging system generally has no parallax in the transverse scanning direction. An embodiment of a dual-energy X-ray imaging system is described in more detail below in connection with FIG. 2.

The image 20 allows for the identification of different portions or regions of interest in the imaged body. For example, an android region 22 of the imaged body can be determined using the image 20. For example, based on tissue information of the imaged body, the android region 22 can be identified and the visceral fat mass thereof estimated or calculated using the acquired tissue information. A lower boundary 24 and an upper boundary 26 of the android region 22 may be determined and identified using information acquired during the dual-energy X-ray scan, including the image 20 and tissue information, including fat and lean tissue information. The android region 22 generally corresponds to the abdominal region or abdomen of a subject.

In general, the image 20 formed from the dual-energy X-ray imaging system is a two-dimensional (2D) image of a three-dimensional (3D) body. In particular, the image 20 is an anterior-posterior (AP) image of a body acquired using a dual-energy X-ray imaging system. The image 20 may also be referred to as a posterior-anterior (PA) image of the body. The dual-energy X-ray imaging system may be used to acquire both bone and tissue information (particularly soft tissue information) from one or more projection measurements of X-ray attenuation at two different X-ray energy ranges. For example, when a subject is lying down on a table between an X-ray source below the subject and an X-ray detector above the subject (or vice versa), the X-ray detector can obtain information for a dual-energy X-ray absorptiometry (DXA) AP view of the composition of the body, including tissue, as well as the spine, bones or portions thereof as a result of the passage of X-rays at two different energy levels through the subject. In an exemplary embodiment, the subject may be a human patient (i.e., a patient), an animal or an object.

Figure 2:
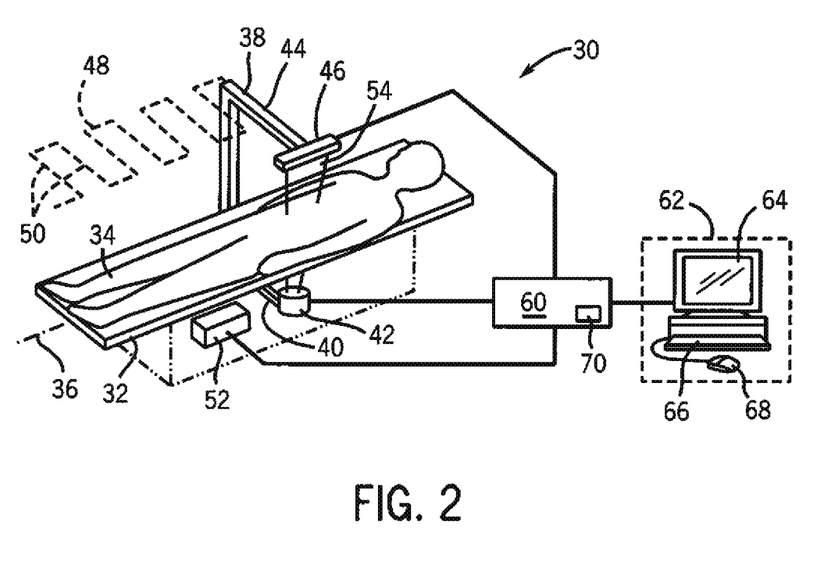
FIG. 2 is a schematic diagram of an exemplary embodiment of a dual-energy X-ray imaging system that may be used to acquire the dual-energy X-ray image of FIG. 1.

FIG. 2 illustrates a schematic diagram of an exemplary embodiment of a dual-energy X-ray imaging system, illustrated as a dual X-ray absorptiometry (DXA) system 30, which may also be referred to as dual-energy bone densitometry system capable of performing bone densitometry. The system 30 is constructed in accordance with various embodiments and is configured to provide for measurement of at least soft tissue composition (body composition), including tissue thickness, an area of a bone, a length of a bone, a bone mineral content (BMC), and a bone mineral density (BMD). The BMD is calculated by dividing the BMC by the area of the bone. During operation, two X-ray beams having different energy levels are utilized to scan an subject, for example, to scan a body of a human patient (e.g., a patient) to image the body of the subject. The acquired image(s), including tissue and bone information from the imaged body, particularly determined tissue composition (body composition) and tissue thickness information, is used to calculate a visceral fat mass of the abdominal region of the subject. The image(s) may be generated in part from determined tissue information and bone density information acquired during a dual-energy X-ray scan.

The dual-energy X-ray imaging system 30 includes a table 32 providing a horizontal surface for supporting a subject 34, for example a patient, in a supine or lateral position along a longitudinal axis 36. The dual-energy X-ray imaging system 30 also includes an imaging assembly 38, for example, such as a C-arm. The imaging assembly 38 includes a lower arm 40 that is positioned beneath the table 32 and supports an X-ray source 42 positioned at one end thereof. The imaging assembly 38 also includes an upper arm 44 that is positioned above the table 32 and supports an X-ray detector 46 at one end thereof. The imaging assembly 38 is configured such that the lower arm 40 and the upper arm 44 are coupled together so that the X-ray source 42 and the X-ray detector 46 move in unison with each other. However, it should be noted that the position of the X-ray source 42 and the X-ray detector 46 may be reversed. The X-ray detector 46 may be fabricated, for example, as a multi-element cadmium-zinc-telluride (CZT) detector providing for energy discrimination. The X-ray source 42 and the X-ray detector 46 may be moved in a transverse raster pattern 48 so as to trace a series of transverse scans 50 of the subject 34, where the X-ray source 42 and the X-ray detector 46 move from side-to-side, perpendicular to longitudinal axis 36, along the entire length of the subject 34, during which dual-energy X-ray imaging data is collected by the X-ray detector 46. Dual-energy X-ray imaging data is collected only during transverse (side-to-side) movement of the X-ray source 42 and the X-ray detector 46. The transverse raster motion is produced by actuators (not shown) under control of a translation controller 52. During operation, the X-ray source 42 produces an X-ray fan beam 54 in a plane that is parallel to the longitudinal axis 36. However, in some embodiments, the X-ray fan beam 54 may be provided in a plane that is perpendicular to the longitudinal axis 36. The transverse raster pattern 48 is adjusted in some embodiments such that there is some overlap (e.g., slight overlap of approximately 10 percent) between successive transverse scans 50 of the X-ray fan beam 54.

In other dual-energy X-ray imaging systems, the X-ray source and the X-ray detector may be moved in a longitudinal raster pattern so as to trace a series of longitudinal scans of the subject, where the X-ray source and the X-ray detector move from head to feet and vice versa, parallel to the longitudinal axis along the entire length of the subject.

The X-ray source 42, the X-ray detector 46, and the translation controller 52 communicate with and are under the control of a computer 60 which may include both dedicated circuitry and one or more processors having the ability to execute a stored program, for example, instructions for computer 60 that are stored in memory or in software. In an exemplary embodiment, the computer 60 also includes a body fat measurement module 70. The body fat measurement module 70 utilizes the dual-energy X-ray image data, and in particular, the acquired tissue and bone information to determine an amount of visceral fat, and more particularly, abdominal visceral fat of a scanned body of the subject 34. During operation, the body fat measurement module 70 directs the dual-energy X-ray imaging system 30 to acquire a scan of a portion of the body or a full body (or total body scan), from which tissue information as well as bone information may be identified. The locations of bone landmarks may be determined automatically, manually or semi-automatically, for example, with an operator adjusting automatically generated landmarks and used to identify regions of interest of the imaged body.

The body fat measurement module 70 may then utilize the dual-energy X-ray image data, including the acquired tissue information, particularly, soft tissue information, and bone information to determine the visceral fat mass in one or more regions of interest of the subject. In various embodiments, using tissue and bone information or measurements in combination with different methods or models, abdominal visceral fat is determined as described in more detail below. It should be noted that different landmarks may be used to identify one or more regions of interest for which the visceral fat mass is to be determined. It also should be noted that different methods or models may be used to determine the visceral fat mass in different sections of the 2D planar image(s) from the dual-energy X-ray imaging system 30. It further should be noted that although the various embodiments are described in connection with a dual-energy X-ray imaging system, the various embodiments are not limited to a dual-energy X-ray imaging system or a particular configuration thereof.

Referring again to FIG. 2, the computer 60 communicates with a terminal, such as a workstation 62 including a display 64, a keyboard 66, and a cursor control device such as a mouse 68 allowing for operator input and the output of text and images to the operator. In some embodiments, the computer 60 is located remotely from the workstation 62. Optionally, the computer 60 may form a portion of the workstation 62. The computer 60 is adapted to perform one or more processing operations. The acquired tissue and bone information, for example, image, density and thickness information may be processed and displayed in real-time during a scanning session as the data is received. Additionally or alternatively, the data may be stored temporarily in a memory device on the computer 60 during a scanning session and then processed and displayed in an off-line operation. The information may also be stored in a long-term storage device (e.g., hard drive or server) for later access, such as during a follow-up scan of the same subject, allowing monitoring of changes in the visceral fat mass of the subject. The display 64 may include one or more monitors that present subject information, including the scanned image, which may include presenting tissue and bone information to the operator for review, diagnosis and/or analysis. The displayed images may be modified and the display settings of the display 64 also may be manually adjusted using the keyboard 66, the mouse 68, or a touch screen icon on the display itself.

During operation, the dual-energy X-ray imaging system 30 may be configured to operate in either a dual-energy X-ray mode or a single energy X-ray mode. In the single energy X-ray mode, the X-ray source 42 emits X-rays in a narrow band of energies of a few keV and in the diagnostic imaging range of approximately 20-150 keV. In the dual-energy X-ray mode, the X-ray source 42 emits radiation in two or more bands of energy emitted simultaneously or in rapid succession. The X-ray source 42 may also be configured to emit a single broadband of energy of more than a few keV over the diagnostic imaging range. The dual-energy X-ray imaging system 30 may be switched between the dual-energy X-ray mode and the single energy X-ray mode by increasing or decreasing the X-ray source 42 voltage and/or current. The dual-energy X-ray imaging system 30 may also be switched between the dual-energy X-ray mode and the single energy X-ray mode by removing or adding a K-edge filter. It should be noted that the X-ray source 42 may emit X-rays at different energies or ranges of energies.

The X-ray source 42 may be configured to output a fan beam of X-rays 54 as shown in FIG. 2. The X-ray source 42 may also be configured to output a thin beam of X-rays (not shown), a cone beam of X-rays, or other configurations. In some embodiments, the body fat measurement module 70 controls the dual-energy X-ray imaging system 30 to operate in the single energy X-ray mode or dual-energy X-ray mode to acquire tissue and bone information to determine the visceral fat mass of one or more portions or regions of a subject. The dual-energy X-ray mode allows the acquisition of both tissue information and skeletal bone information, for example, soft tissue information, such as fat density or fat thickness information. Accordingly, the dual-energy X-ray mode allows for both soft tissue and skeletal imaging of the subject 34 using attenuation information from different energy levels. It should be noted that in the single energy X-ray mode, higher resolution images also may be generated.

Various embodiments provide for calculating or estimating the visceral fat mass of one or more different portions or regions of a subject. The tissue and bone information used for calculating the visceral fat mass is acquired in the various embodiments using a one or more dual-energy X-ray scans. For example, region specific X-ray scans may be performed where only a portion or region of the subject 34 (e.g., the abdominal region) is scanned for use in calculating the visceral fat mass. In other embodiments, a full body or total body X-ray scan is performed.

Figure 3:
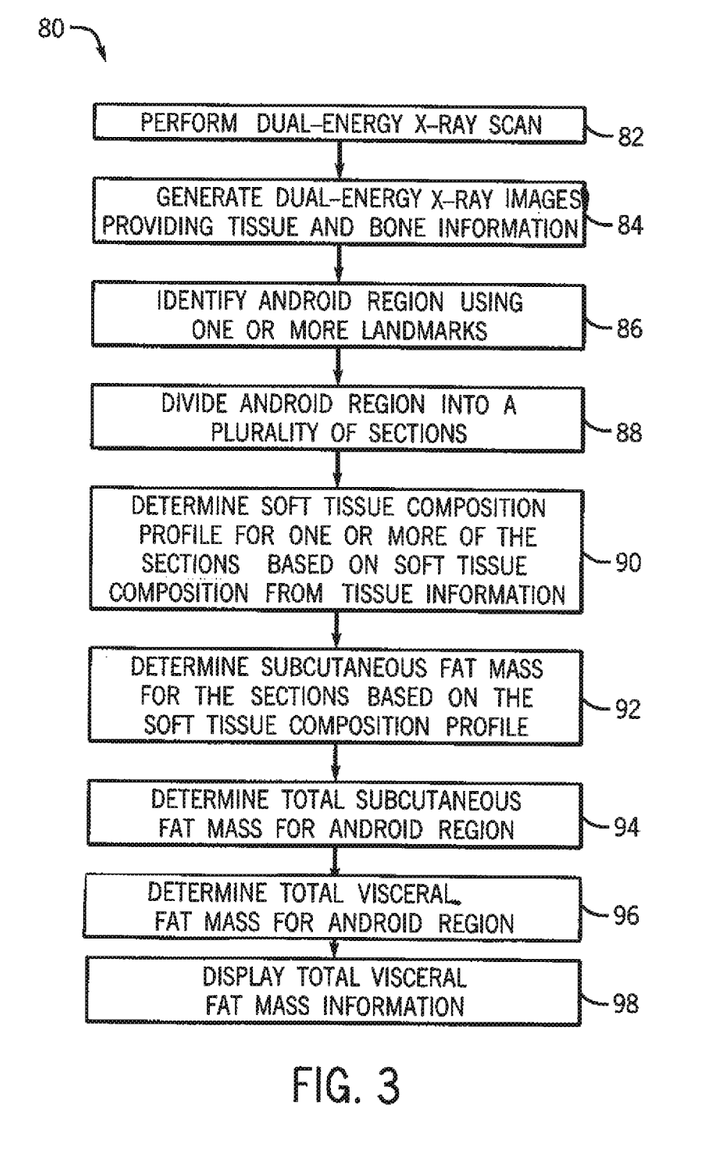
FIG. 3 is a flow diagram of an exemplary embodiment of a method for calculating the visceral fat mass of a subject.

FIG. 3 illustrates a flow diagram of an exemplary embodiment of a method 80 for calculating the visceral fat mass of a subject. It should be noted that although the method 80 and the various embodiments are described in connection with calculating the visceral fat mass for a particular body volume or body part, for example, for the android region or abdomen, the method 80 and the various embodiments may be used to calculate the visceral fat mass for any portion of an imaged body. In some embodiments, and as described in more detail below, the method 80 uses a planar dual-energy X-ray imaging system to segment visceral fat in the abdomen.

The method 80 includes performing a dual-energy X-ray scan of a subject, such as a patient or a portion of a patient at step 82. The subject in some embodiments lies supine on a table of a dual-energy X-ray imaging system, such as a bone densitometry system. However, in other embodiments, the subject may be imaged with a dual-energy X-ray imaging system while the subject is in a standing position or other position.

The dual-energy X-ray scan may be a rectilinear scan of a portion of the subject or of the entire body of the subject, which may be performed in a raster-type scanning sequence as described in more detail herein. During the dual-energy X-ray scan, an image of a portion of or the entire subject may be acquired, which includes tissue information, from which soft tissue composition may be determined, and bone information relating to the bones in the skeleton. For example, a dual-energy X-ray detector receives X-ray radiation after an X-ray beam has passed through the subject and generates electrical signals indicating the attenuation of the X-ray radiation through the subject within distinct first and second energy ranges. Images such as a bone density images, tissue images, particularly soft tissue images, or a combination thereof are produced based on the attenuation of the X-ray radiation in the first and second energy ranges. Thus, the dual-energy X-ray imaging system allows not only the formation of a radiographic attenuation image, but also the mathematical analysis of the composition of the attenuating material by dual-energy X-ray imaging techniques. For example, dual-energy X-ray imaging techniques may be used to quantitatively compare the attenuation of X-ray radiation at two energies to distinguish between bone and soft tissue, as well as to distinguish between different types of tissue, for example, different types of fat as described in more detail herein. In various embodiments, the dual-energy X-ray scan acquires dual-energy 2D (planar) imaging information.

It should be noted that a full body or total body scan of an entire body may be performed as a single scanning operation. The full body or total body scan may be a low dose mode imaging scan. In some embodiments, instead of a full body or total body scan, individual smaller scans of a region of interest, for example, the android region of a subject, may be performed in single sweep or in a series of rectilinear scans.

Referring again to method 80, after performing the dual-energy X-ray scan of a subject, one or more dual-energy X-ray images of the subject are generated at step 84, with each image containing at least one of bone information, for example, bone image information and bone content information, as well as soft tissue information, for example, fat content or fat mass or thickness information, thereby providing soft tissue composition information. For example, an image 20 as shown in FIG. 1 may be generated from an imaging scan of the entire body, the image 20 including soft tissue information. Bone and soft tissue information may be separately identified, for example, by setting different attenuation thresholds, such as an attenuation range that defines bone, soft tissue and air. The settings may be predetermined, determined by a operator or adjusted by a operator. Alternatively, one or more dual-energy X-ray images of a region of interest may be generated, which are smaller than the full body dual-energy X-ray image 20.

Figure 4:
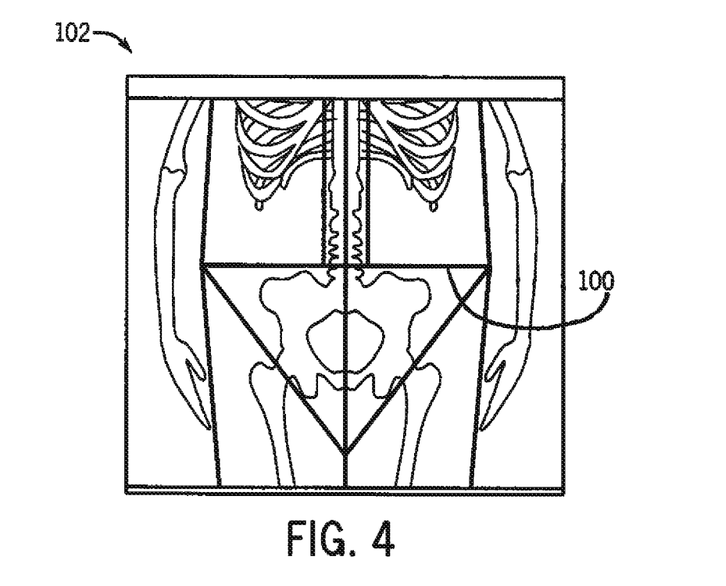
FIG. 4 is a diagram of an exemplary embodiment of a dual-energy X-ray bone image illustrating a landmark used to identify an abdominal region of a subject.
Figure 5:
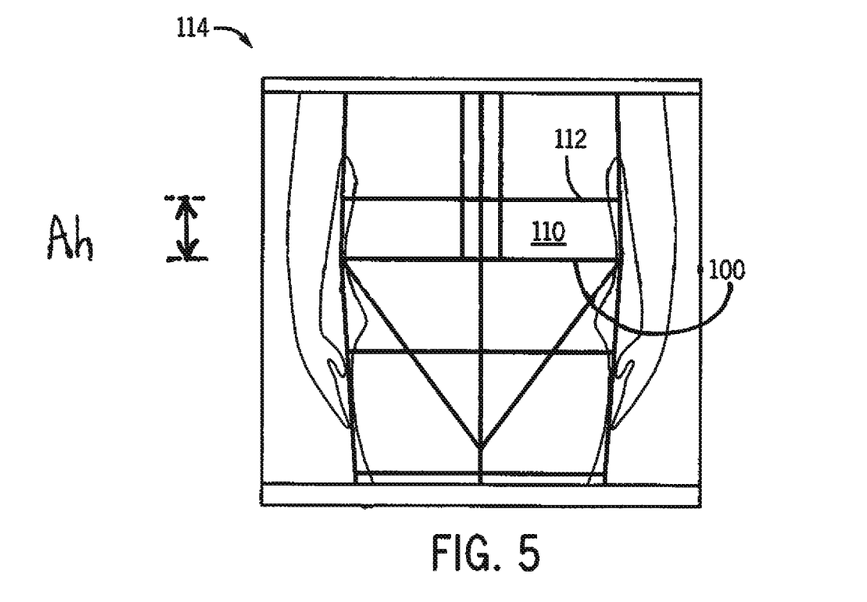
FIG. 5 is a diagram of an exemplary embodiment of a dual-energy X-ray tissue image identifying an abdominal region of a subject.

FIG. 4 illustrates a diagram of an exemplary embodiment of a dual-energy X-ray bone image illustrating a landmark used to identify an abdominal region of a subject, while FIG. 5 illustrates a diagram of an exemplary embodiment of a dual-energy X-ray tissue image identifying an abdominal region of a subject. Using one or more dual-energy X-ray images, for example, the images shown in FIGS. 4 and 5, a region of interest, which in various embodiments may be the android region, abdominal region or abdomen of a subject, may be identified by using one or more landmarks at step 86 of method 80 in FIG. 3. For example, landmarks may be identified that allow for locating one or more scan lines that encompass a region of interest, such as the android region. It should be noted that the dual-energy X-ray image may be composed of data from X-ray radiation detected by discrete pixels within the dual-energy X-ray detector. Bone density and soft tissue information may be determined from information corresponding to attenuation of the X-ray radiation in each of the discrete pixels of the dual-energy X-ray detector. This bone density and soft tissue information may be mapped to a gray scale to present images to an operator of the dual-energy X-ray imaging system.

The landmarks may correspond to different regions of interest and may be determined automatically, manually or semi-automatically. In an exemplary embodiment, landmarks may be identified to determine portions of images portions that correspond to an android region of a subject. It should be noted that the landmarks are not limited to a particular kind or type of landmark, for example, a bone, but may be an area defined by soft tissue or other body elements. As an example, in embodiments where an android region is to be identified, the various embodiments may identify the top of the iliac crest of the pelvis, identified in image 102 of FIG. 4 by the line 100, as determined from an imaged pelvis bone from a dual-energy X-ray scan as shown. The iliac crest is the thick curved upper border of the ilium, the most prominent bone in the pelvis of a human body.

The identification of the iliac crest may be performed in different ways. For example, the iliac crest may be determined manually by an operator viewing a full body dual-energy X-ray image and placing a line (e.g., using a mouse) at the region of the image where the iliac crest is observed. It should be noted that the line may be defined by two endpoints or may be generated and then increased or decreased in length as needed, as well as moved or adjusted. The iliac crest also may be identified automatically using any method, for example, a template matching method or by searching for the widest bone structure in the hip region and identifying the top of that bone structure. It should be noted that when the automatic identification method is used, a operator may still adjust the identified location of the iliac crest, for example, by moving an automatically generated line. Therefore, it should be noted that any method may be used to determine the iliac crest and the identification thereof is not limited to the methods described above.

As shown in FIG. 5, the android region 110 may be determined from the top of the iliac crest. The android region 110 generally defines an abdominal region of interest for which measurement of visceral fat mass is accordance with various embodiments is performed. For example, the android region 110 as shown in image 114 of FIG. 5 may be defined between line 100, identifying the top of the iliac crest and line 112, which is defined by a predetermined distance from line 100. In an exemplary embodiment, the distance from line 100 (i.e., the top of the iliac crest) to the top of android region 110 at line 112 may be calculated by measuring the distance from the top of the iliac crest to the bottom of the skull of the subject and multiplying that distance by 0.2. In other words, the distance between line 100 and line 112 is defined as twenty percent (20%) of the distance from the top of the subject's iliac crest to the bottom of the subject's skull. The height of the android region 110, the distance between line 100 and line 112, is also defined as the android height, identified in FIG. 5 as Ah. It should be noted that the distance between line 100 and line 112 (i.e., the android height Ah) may also be determined from bone information from a full body scan using a pixel counting method between the two landmarks. In the pixel counting method, the distance from the top of the iliac crest to the bottom of the skull is measured using a pixel count as each pixel in the full body dual-energy X-ray image has a known size in vertical and horizontal directions. In other embodiments, line 112 may be defined by a predetermined distance from line 100, for example, ten centimeters, fifteen centimeters, etc. It should also be noted that the distance between line 100 and line 110 may be based in part on certain characteristics of the patient, for example, patient height, patient age, etc.

Figure 6:
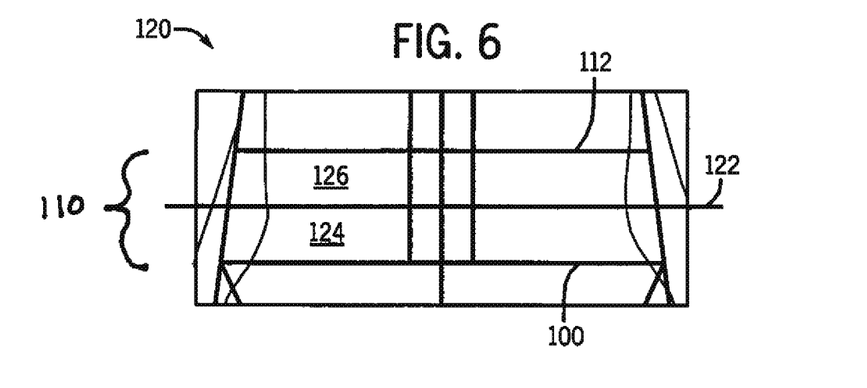
FIG. 6 is a diagram of an exemplary embodiment of a dual-energy X-ray tissue image identifying an abdominal region of a subject and illustrating different sections used to determine a visceral fat mass of the subject.

Referring again to method 80, once the android region 110 is identified at step 86, the android region 110 is divided into a plurality of sections at step 88. FIG. 6 illustrates a diagram of an exemplary embodiment of a dual-energy X-ray tissue image identifying an abdominal region of a subject and illustrating different sections used to determine a visceral fat mass of the subject. In the image 120 of FIG. 6, the android region 110 is divided by a line 122, which may be defined and generated by an operator or automatically defined and generated by the dual X-ray imaging system, into two halves, namely, a bottom half or inferior section 124 and a top half or superior section 126. The method of the present disclosure treats the inferior section 124 and superior section 126 somewhat differently. The superior section 126 typically, but not always, is above the buttocks of a subject, and the inferior section 124 includes the buttocks of the subject. It should be noted that the android region 110 may be divided into more than two sections. Additionally, the sections into which the android region 110 is divided may be equal in size or unequal in size.

Figure 7:
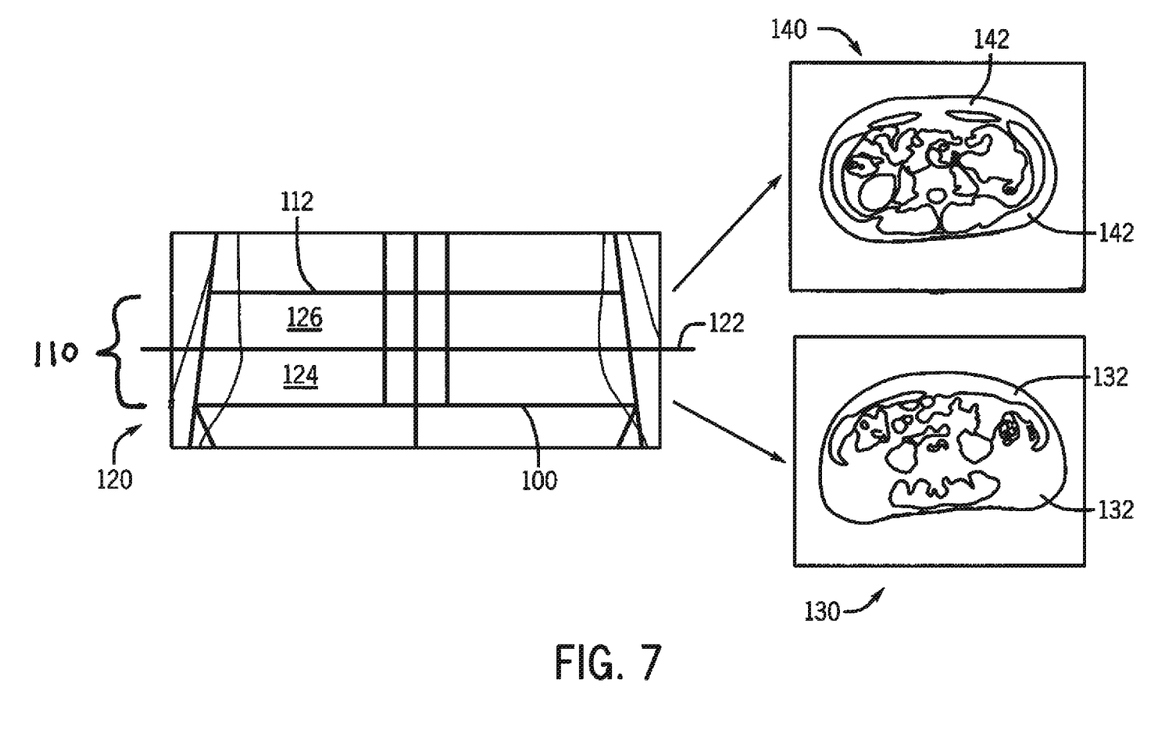
FIG. 7 is a diagram of the dual-energy X-ray tissue image of FIG. 6 with two additional cross-sectional computed tomography (CT) images illustrating different body compositions at different sections of the abdominal region of a subject.

Thereafter, a soft tissue composition profile is determined at step 90 for one or more of the inferior sections 124 or superior sections 126 based on acquired soft tissue composition information, for example, soft tissue information from the imaged body of a subject. The body composition at different sections of the abdomen, including the soft tissue profile for each of the sections is different as illustrated FIG. 7. FIG. 7 illustrates a diagram of the dual-energy X-ray tissue image of FIG. 6 with two additional cross-sectional computed tomography (CT) images illustrating different body compositions at different sections of the abdominal region of a subject. In particular, image 130 illustrates the body composition of inferior section 124 and image 140 illustrates the body composition of superior section 126. Therefore, FIG. 7 illustrates the differences in body composition between inferior section 124 and superior section 126. It should be noted that these cross-sectional CT images were not generated by a dual-energy X-ray imaging system, which as described above generates one or more 2D planar images of a body in the AP or PA direction. However, using a dual-energy X-ray imaging system, images with bone information and soft tissue information may be displayed, and body composition, including tissue thickness or fat thickness may be determined as described herein. The images 130 and 140 illustrate that the amount of fat, for example, the amount of subcutaneous adipose tissue (SAT) 132 and 142 in each of the images, respectively. In particular, image 130 is an image of inferior section 124 and image 140 is an image of superior section 126. As can be seen in FIG. 7, there is a larger amount of SAT 132 in inferior section 124 than the amount of SAT 142 in superior section 126. The larger amount of SAT 132 in inferior section 124 is typically due to the buttocks of the subject.

Figure 8:
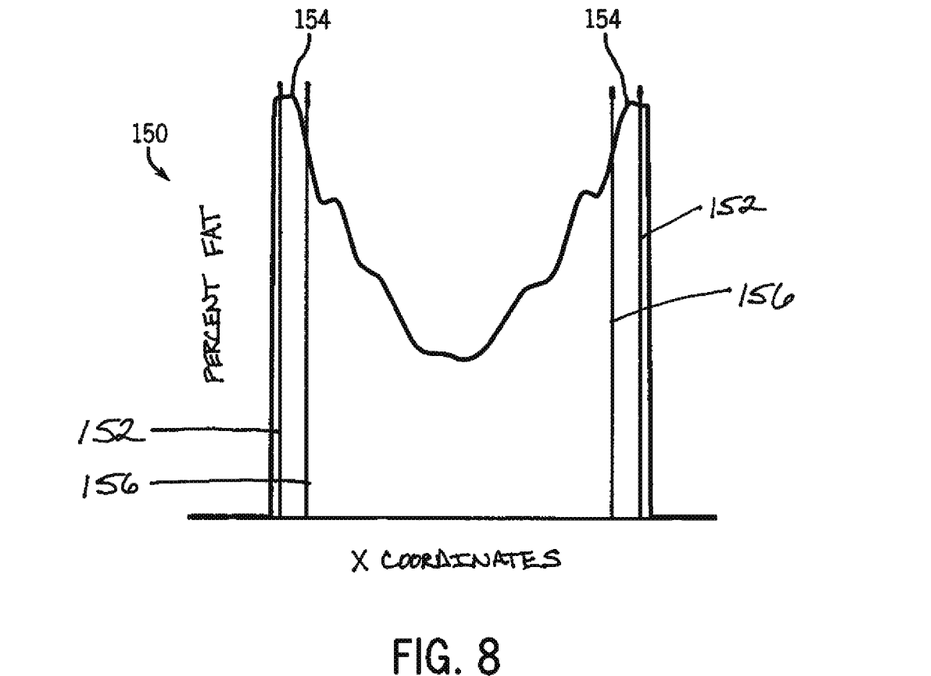
FIG. 8 is an exemplary embodiment of a soft tissue composition profile of the abdominal region of a subject.

FIG. 8 illustrates an exemplary embodiment of a soft tissue composition profile 150 of the abdominal region of a subject. A separate soft tissue composition profile is generated for each of the inferior and superior sections. The soft tissue composition profile 150 may be generated from the soft tissue information, including soft tissue thickness information and identifies the soft tissue thickness or fat thickness or mass across one or more lines of a scanned body. The soft tissue composition profile 150 illustrates that the fat thickness or mass is generally greater at the edges of the body identified by lines 152 than in the middle of the body. The soft tissue composition profile 150 shows the change in fat thickness or mass of the soft tissue based on, for example, the change in attenuation of X-ray radiation through the body. It should be noted that the values for the soft tissue composition profile 150 is an average composition over the vertically integrated scan lines for all horizontal positions, for example, over the entire body or one of the sections. Accordingly, the soft tissue composition profile 150 is a composition distribution in the horizontal direction, namely from side-to-side across the entire body. The soft tissue composition profile 150 has two peaks 154 at both ends that represent the subcutaneous fat layer.

For each side of the body, the left and right sides, the average start of the abdomen over all lines in the inferior and superior sections is found. A very low tissue threshold is used to find the edge of the body (i.e., air/tissue boundary) in the image, and the average transition from air to tissue is calculated. The edge of the body (i.e., air/tissue boundary) is identified by lines 152. The outer edge of the abdominal wall of the body is found by looking for the point of highest negative derivative, traveling towards the center from the outer edge. The outer edge of the abdominal wall of the body is identified by lines 156. The average of the distance between the left pair of lines 152 and 156, and the right pair of lines 152 and 156 is used to estimate the subcutaneous fat layer thickness.

Returning to method 80, the subcutaneous fat mass for each of the inferior and superior ections is determined at step 92 based on the soft tissue composition profile 150. It should be noted that in various embodiments the subcutaneous fat mass is determined differently for each inferior section 124 and superior section 126. Specifically, as can be seen from FIG. 8, the distribution of the soft tissue composition profile 150 includes two peaks 154 at both ends that represent the subcutaneous fat layer. The subcutaneous fat layer thickness is then measured by thresholding the soft tissue composition profile 150. For example, for each side, the peak is specifically identified. The minimum of the profile is then determined. The threshold is then set at a predetermined value from the minimum to the maximum (peak), for example, set at the point of maximum derivative, as illustrated by lines 156. Accordingly, the initial calculated thickness of the subcutaneous fat mass is the distance from the threshold to the end of the profile (between lines 156 and 152 in FIG. 8), which is then multiplied by an empirically derived constant. The constant may be derived based on empirical studies or simulations. This multiplication operation is performed because the threshold value will not necessarily correspond exactly to the inner extent of the subcutaneous fat region, because the threshold value is the edge of a circular region. In various embodiments, the average of the final calculated thickness for the left and right sides of the body is used for estimating the subcutaneous fat mass. Thus, virtual calipers defined by the threshold values are used to define the thickness of the subcutaneous fat layer at the perimeter of the android region.

Figure 9:
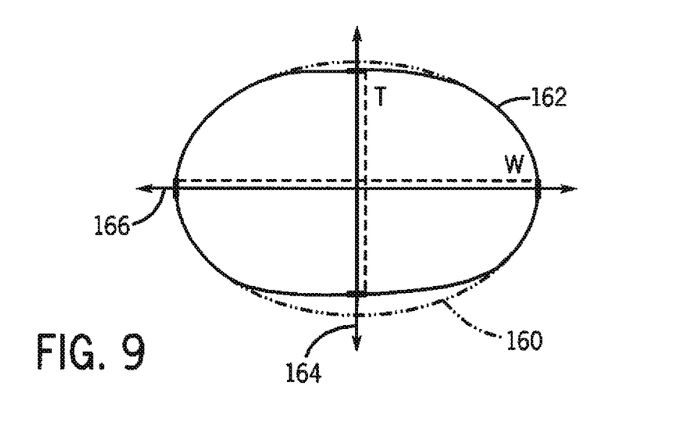
FIG. 9 is an exemplary embodiment of a diagram illustrating the use of an elliptical model to approximate the cross-section of an imaged section of an abdominal region of a subject to determine the visceral fat mass of the subject.

FIG. 9 illustrates an exemplary embodiment of a diagram illustrating the use of an elliptical model to approximate the cross-section of an imaged section of an abdominal region of a subject to determine the visceral fat mass of the subject. The android region 110 of a subject may be approximated by an ellipse 160 as shown in FIG. 9. However, the cross-section of the inferior section 124 or the superior section 126 of the android region 110 may not necessarily have a smooth, consistent and/or regular cross-section. For example, the cross-section of the inferior section 124 or the superior section 126 may have a boundary 162 that is irregular or non-elliptical. In accordance with various embodiments, the height of the ellipse 160 may be determined from the peak thickness of the soft tissue image. In various embodiments, using the soft tissue information from the dual-energy X-ray scan, or the soft tissue composition profile 150, a tissue thickness along one or more scan lines may be determined. For example, using the soft tissue information from the dual-energy X-ray scan, a peak soft tissue thickness of the DXA soft tissue along one or more scan lines may be determined. The peak tissue thickness defines a distance across the imaged body, for example, from an anterior region to a posterior region of the body, which is used as the length of the minor axis (T) 164 of the ellipse 160.

The width of the DXA image at a middle or average portion of the inferior section 124 or the superior section 126 defines the length of the major axis (W) 166 of the ellipse 160. Using a pixel measuring method, the width may be determined as the distance from one side of the imaged body to the other side using a pixel count (as each pixel in the full body dual-energy X-ray image has a known size in the vertical and horizontal direction). The pixel count may start, for example, from a left edge (i.e., air/tissue boundary) of the imaged body and continue to a right edge (i.e., air/tissue boundary) of the imaged body.

The subcutaneous adipose tissue (SAT) or subcutaneous fat mass is determined by the subcutaneous adipose tissue area of the inferior section 124 and superior section 126, which is calculated by taking the subcutaneous adipose tissue thickness and multiplying that value by the circumference of the ellipse 160.

It should be noted that the perimeter or circumference of the ellipse 160 may be determined using mathematical calculations as are known to calculate the perimeter or circumference either exactly or using approximations. Specifically, the perimeter or circumference of the ellipse 160 may be calculated as follows (and as is known): $4aE(\epsilon)$, where the function E is a complete elliptic integral of the second kind. In some embodiments, the perimeter or circumference may be calculated as follows: $(4a)*integral$ (from 0 to $\pi/2$ of sqrt{$(1-k^2(sin(theta))^2$}d(theta)), where k={sqrt($a^2-b^2$)}/a and a and b are the axes 166 and 164, respectively.

The perimeter or circumference may be also be approximated as the perimeter of the ellipse as follows: $2(\pi)sqrt\{(a^2+b^2)/2\}$, where a and b are the axes 166 and 164, respectively. It should be noted that any method known in the art may be used to calculate the perimeter or circumference of the ellipse 160.

Having determined the SAT area of the superior section 126, the SAT area of the inferior section 124 is determined in a different manner. In particular, in various embodiments, the SAT area of the inferior section 124 is determined using the ellipse 160. The inferior section 124 fat mass is determined by using the fat thickness at the threshold point multiplied by half the ellipse 160 width w divided by 2, however, the anterior portion of the ellipse's 160 thickness is used from the thickness value of the superior section 126, and the posterior portion of the ellipse's 160 thickness is calculated based on the tissue information for the inferior section 124 using the method described above. Thus, the anterior portion of the inferior section 124 is closely modeled by copying the elliptical parameters from the superior section 126. The various embodiments implement this method as the anterior portion of the abdomen is quite uniform from the superior side to the inferior side of the android region, while the posterior portion of the abdomen is not.

It should be noted that different methods may be used to calculate the SAT area of the different sections and are not limited to the methods described above. For example, different profiles or models may be used for each of the sections.

Referring again to the method 80, the total subcutaneous fat mass is determined at step 94 based on the determined subcutaneous fat thickness and total fat thickness (from the dual-energy X-ray image scan). In particular, the total subcutaneous fat mass is calculated by adding up the elliptical cross sections for each of the sections, for example, the inferior section 124 and superior section 126. The subcutaneous fat mass is the area times the height of the region of interest.

Figure 10:
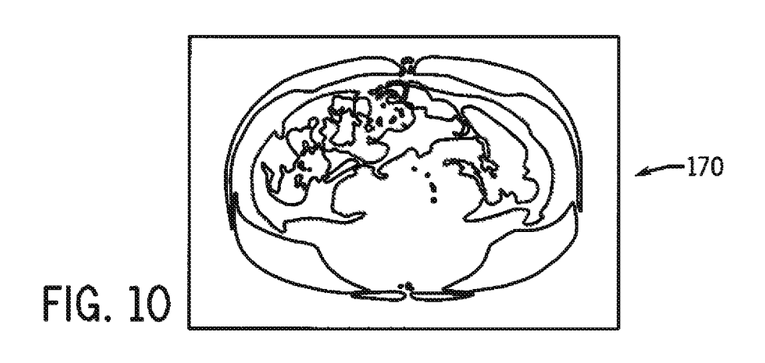
FIG. 10 is an exemplary embodiment of a cross-sectional CT image illustrating the total fat in an abdominal region of a subject.
Figure 11:
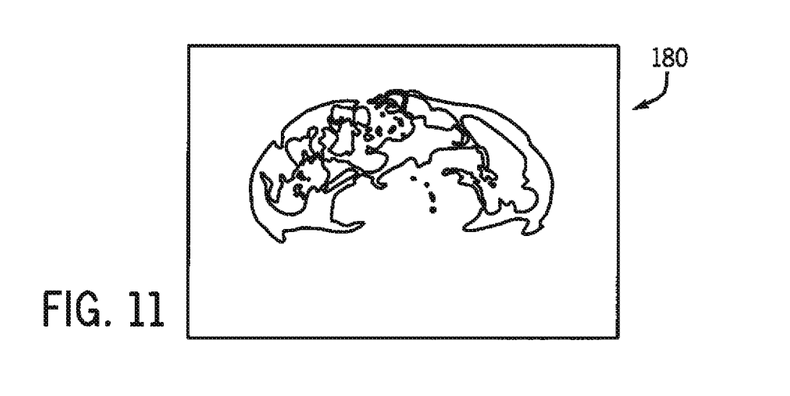
FIG. 11 is an exemplary embodiment of a cross-sectional CT image illustrating the visceral fat in an abdominal region of a subject after removal of the subcutaneous fat from the image.

The total visceral fat mass is determined at step 96. Specifically, the total visceral fat mass is the total fat in the abdomen, which may be determined from the tissue information from the DXA scan, and as shown in the image 170 of FIG. 10, minus the total subcutaneous fat mass calculated as described above. FIG. 10 illustrates an exemplary embodiment of a cross-sectional CT image illustrating the total fat in an abdominal region of a subject. The total visceral fat mass is represented by image 180 in FIG. 11, which is the total fat mass minus the calculated total subcutaneous fat mass. FIG. 11 illustrates an exemplary embodiment of a cross-sectional CT image illustrating the visceral fat in an abdominal region of a subject after removal of the subcutaneous fat from the image. A total visceral fat mass value and/or a total subcutaneous fat mass value may be displayed, for example, adjacent to or with the dual-energy X-ray image. It should be noted that individual visceral fat values and/or subcutaneous fat values for each inferior and/or superior section may also be separately displayed.

Thus, various embodiments of the disclosure use DXA technology to measure the soft tissue composition in a planar image of the abdomen, and then measure the subcutaneous fat thickness on the sides of the body to calculate the subcutaneous fat mass. The subcutaneous fat mass is then subtracted from the total abdominal fat mass to yield the visceral fat mass. The DXA image of the abdomen is a planar 2D image that does not specifically identify where the fat lies in the vertical plane. The DXA image does measure total abdominal fat. The thickness of the subcutaneous fat layer, which surrounds the midriff, is measured using the soft tissue composition profile. As the thickness is known, the volume of subcutaneous fat may be determined or estimated by assuming an elliptical cross-section for the subcutaneous fat. The value of the volume of the subcutaneous fat mass is then subtracted from the total fat mass in the abdomen to yield the visceral fat mass.

While the disclosure has been described with reference to various embodiments, those skilled in the art will appreciate that certain substitutions, alterations and omissions may be made to the embodiments without departing from the spirit of the disclosure. Accordingly, the foregoing description is meant to be exemplary only, and should not limit the scope of the disclosure as set forth in the following claims.

What is claimed is:

1. A method for determining visceral fat mass of a body, the method comprising:
   performing a dual-energy X-ray scan of a body;
   generating at least one dual-energy X-ray image of the body from the dual-energy X-ray scan of the body;
   identifying a region of interest on the at least one dual-energy X-ray image of the body for determining visceral fat mass of the body;

wherein the region of interest is separated into a superior section and an inferior section;

determining a subcutaneous fat mass for each of the superior section and the inferior section of the region of interest; and determining a visceral fat mass for the region of interest based on the determined subcutaneous fat mass for each of the superior section and the inferior section;

wherein each of the superior section and the inferior section is separated into an anterior portion and a posterior portion.

2. The method of claim 1, further comprising estimating the subcutaneous fat mass for the superior section and inferior section using at least two different models and methods.

3. The method of claim 2, further comprising using a model for a cross-section of the superior section to determine the subcutaneous fat mass.

4. The method of claim 3, wherein the model uses tissue information from the anterior portion and the posterior portion of the superior section of an android region of the body.

5. The method of claim 3, wherein the model uses tissue information from the anterior portion and the posterior portion of the inferior section of an android region of the body.

6. The method of claim 3, wherein the model uses tissue information from the superior section including tissue information from the anterior portion and the posterior portion of the the superior section, and the inferior section including tissue information from the anterior portion and posterior portion of the the inferior section.

7. The method of claim 3, wherein a height of the model is determined from a peak tissue thickness for the cross-section and a width of the model is determined from a width of the dual-energy X-ray image at the cross-section.

8. The method of claim 1, wherein the superior section and the inferior section include body portions in the region of interest having a similar size.

9. The method of claim 1, wherein the sections superior section and the inferior section include body portions in the region of interest having a different size.

10. The method of claim 1, wherein the region of interest is an android region of the body.

11. The method of claim 10, further comprising identifying the android region using bone information from the dual-energy X-ray image.

12. The method of claim 11, further comprising identifying the android region using a top of an iliac crest bone of the body.

13. The method of claim 12, wherein the android region is defined as a region above the top of the iliac crest bone for a distance that is defined by twenty percent (20%) of a distance from the top of the iliac crest bone to a bottom of a skull of the body.

14. The method of claim 1, further comprising generating a soft tissue composition profile for the superior section and the inferior section for use in determining the subcutaneous fat mass for each of the plurality of sections.

15. The method of claim 14, further comprising applying thresholding to the soft tissue composition profile to define an area for the superior section and the inferior section.

16. The method of claim 14, wherein the soft tissue composition profile identifies an edge of the body, an outer edge of an abdominal wall of the body, and a subcutaneous fat thickness of the body.

17. The method of claim 1, wherein the dual-energy X-ray scan is a series of transverse raster pattern scans moving from side-to-side across the body.

18. A method for determining visceral fat mass of an abdominal region of a body, the method comprising:

acquiring body composition information using a planar dual-energy X-ray imaging system; and segmenting visceral fat in the abdominal region using the acquired body composition information to determine the visceral fat mass of the body;

generating a soft tissue composition profile from the body composition information to segment the visceral fat; and using virtual calipers on the soft tissue composition profile to define subcutaneous fat regions from which the visceral fat is segmented.

19. The method of claim 18, further comprising using different models to segment the visceral fat.

20. A diagnostic imaging system comprising:

a dual-energy X-ray bone densitometry system configured to acquire body composition information from a dual-energy X-ray scan of a subject; and a body fat measurement module configured to segment visceral fat in an abdominal region of the subject to determine an amount of visceral fat mass in the abdominal region using the body composition information;

wherein the region of interest is separated into a superior section and an inferior section and each of the superior section and inferior section is separated into an anterior portion and a posterior portion.

21. The diagnostic imaging system of claim 20, wherein the body fat measurement module is configured to use different models to segment the visceral fat in the superior section and an inferior section of the abdominal region of the subject.

22. A method for determining visceral fat mass of an abdominal region of a body, the method comprising:

acquiring body composition information using a planar dual-energy X-ray imaging system;

segmenting visceral fat in the abdominal region using the acquired body composition information to determine the visceral fat mass of the body; and segmenting the visceral fat using different anterior and posterior regions of the body.

* * * * *